(12) United States Patent
Yoon et al.

(10) Patent No.: US 12,193,848 B2
(45) Date of Patent: Jan. 14, 2025

(54) METHOD OF DETERMINING REGULARITY OF BIO-SIGNAL, APPARATUS AND METHOD FOR ESTIMATING BIO-INFORMATION

(71) Applicant: SAMSUNG ELECTRONICS CO., LTD., Suwon-si (KR)

(72) Inventors: Seung Keun Yoon, Seoul (KR); Ui Kun Kwon, Hwaseong-si (KR); Young Soo Kim, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 628 days.

(21) Appl. No.: 17/149,905

(22) Filed: Jan. 15, 2021

(65) Prior Publication Data
US 2022/0071568 A1   Mar. 10, 2022

(30) Foreign Application Priority Data
Sep. 10, 2020   (KR) .................. 10-2020-0116088

(51) Int. Cl.
*A61B 5/021* (2006.01)
*A61B 5/00* (2006.01)
(Continued)

(52) U.S. Cl.
CPC ........ *A61B 5/7285* (2013.01); *A61B 5/02108* (2013.01); *A61B 5/0295* (2013.01);
(Continued)

(58) Field of Classification Search
CPC .............. A61B 5/02125; A61B 5/4836; A61B 5/7235; A61B 5/316; A61B 5/4848;
(Continued)

(56) References Cited

U.S. PATENT DOCUMENTS 5,292,348 A    3/1994  Saumarez et al.
5,312,441 A *  5/1994  Mader ................ A61N 1/39622
                                                           607/5
(Continued)

FOREIGN PATENT DOCUMENTS

JP    2003332912 A   11/2003
JP    2009291379 A   12/2009
(Continued)

OTHER PUBLICATIONS

Ernesto F. Treo et al., "Algorithm for identifying and separating beats from arterial pulse records", BioMedical Engineering OnLine, vol. 4, 48, doi: 10.1186/1475-925X-4-48, Aug. 11, 2005, 9 pages total, XP021007809.
Communication dated May 3, 2022 issued by the European Patent Office in counterpart European Application No. 21184478.2.

*Primary Examiner* — Deborah L Malamud
(74) *Attorney, Agent, or Firm* — Sughrue Mion, PLLC

(57) ABSTRACT

A method of determining regularity of a bio-signal is provided. The method of determining regularity of a bio-signal according may include acquiring a plurality of pulse waveforms of the bio-signal, acquiring a plurality of slope waveforms corresponding to the plurality of pulse waveforms, binarizing the plurality of slope waveforms, acquiring synchronization information of the plurality of pulse waveforms based on binarizing the plurality of pulse waveforms; acquiring a synchronization rate of a reference interval based on the synchronization information, and determining whether the bio-signal is regular or irregular based on the synchronization rate of the reference interval.

17 Claims, 17 Drawing Sheets

(51) Int. Cl.
*A61B 5/0295* (2006.01)
*A61B 5/0535* (2021.01)
*A61B 5/11* (2006.01)
*A61B 5/308* (2021.01)
*A61B 5/313* (2021.01)

(52) U.S. Cl.
CPC .......... *A61B 5/0535* (2013.01); *A61B 5/1102* (2013.01); *A61B 5/308* (2021.01); *A61B 5/313* (2021.01); *A61B 5/441* (2013.01); *A61B 5/68* (2013.01)

(58) Field of Classification Search
CPC ... A61B 5/7246; A61B 5/7264; A61B 5/0036; A61B 5/02108; A61B 5/486; A61B 5/7275; A61B 5/02427; A61B 5/24; A61B 5/35; A61B 5/7267; A61N 1/3603; A61N 1/36135; A61N 1/36178; G16H 50/30; G16H 10/60; G16H 50/50; Y10S 388/912
See application file for complete search history.

(56) References Cited

U.S. PATENT DOCUMENTS

| | | | |
|---|---|---|---|
| 6,754,528 | B2 | 6/2004 | Bardy et al. |
| 7,794,406 | B2 | 9/2010 | Reisfeld et al. |
| 7,930,020 | B2 | 4/2011 | Zhang et al. |
| 10,149,621 | B2 | 12/2018 | Yoon et al. |
| 2005/0049470 | A1 | 3/2005 | Terry |
| 2011/0105925 | A1 | 5/2011 | Hatakeyama et al. |
| 2014/0180044 | A1 | 6/2014 | Addison et al. |
| 2018/0085011 | A1* | 3/2018 | Ma .................. A61B 5/14542 |
| 2019/0167200 | A1 | 6/2019 | Jang et al. |
| 2019/0298272 | A1 | 10/2019 | Persen et al. |

FOREIGN PATENT DOCUMENTS

| | | |
|---|---|---|
| JP | 2016202462 A | 12/2016 |
| KR | 1020090001146 A | 1/2009 |
| KR | 1020150094256 A | 8/2015 |
| KR | 10-2019-0065115 A | 6/2019 |
| KR | 1020190130925 A | 11/2019 |
| WO | 2018/137300 A1 | 8/2018 |

* cited by examiner

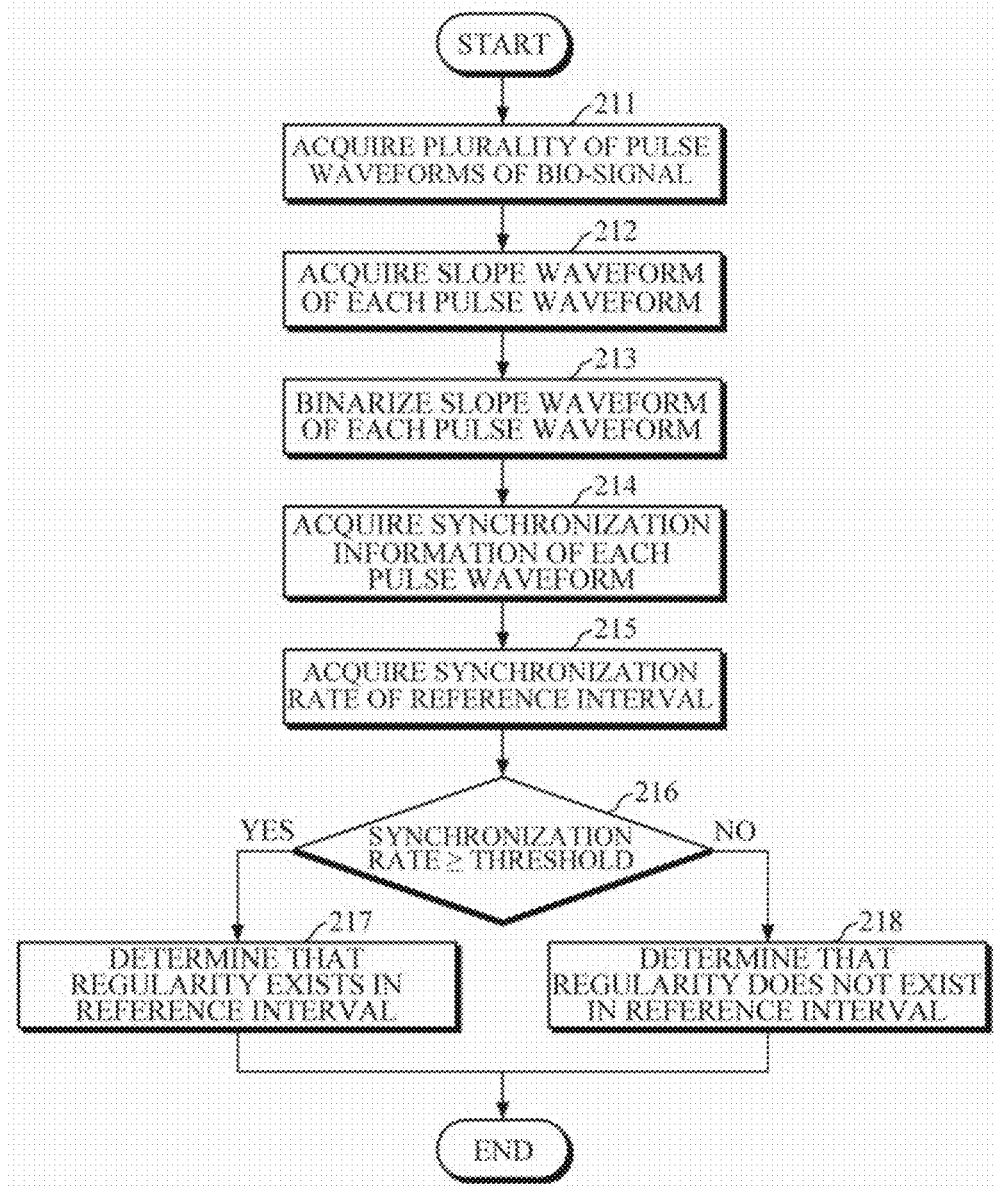

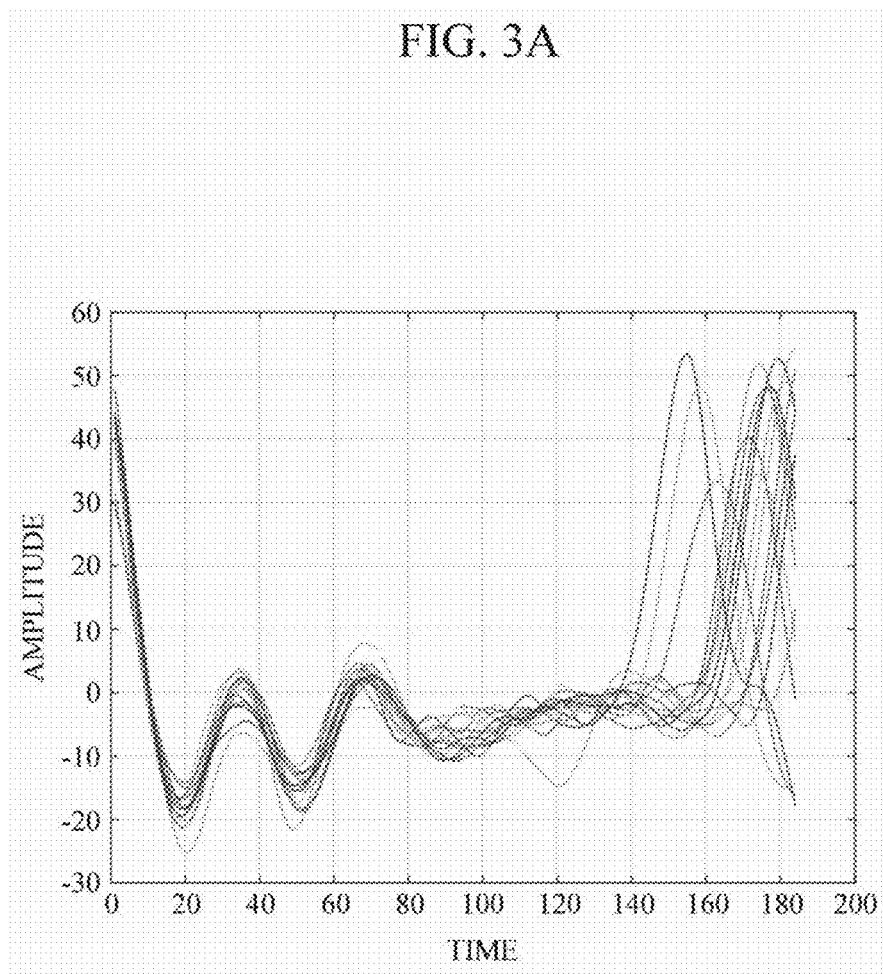

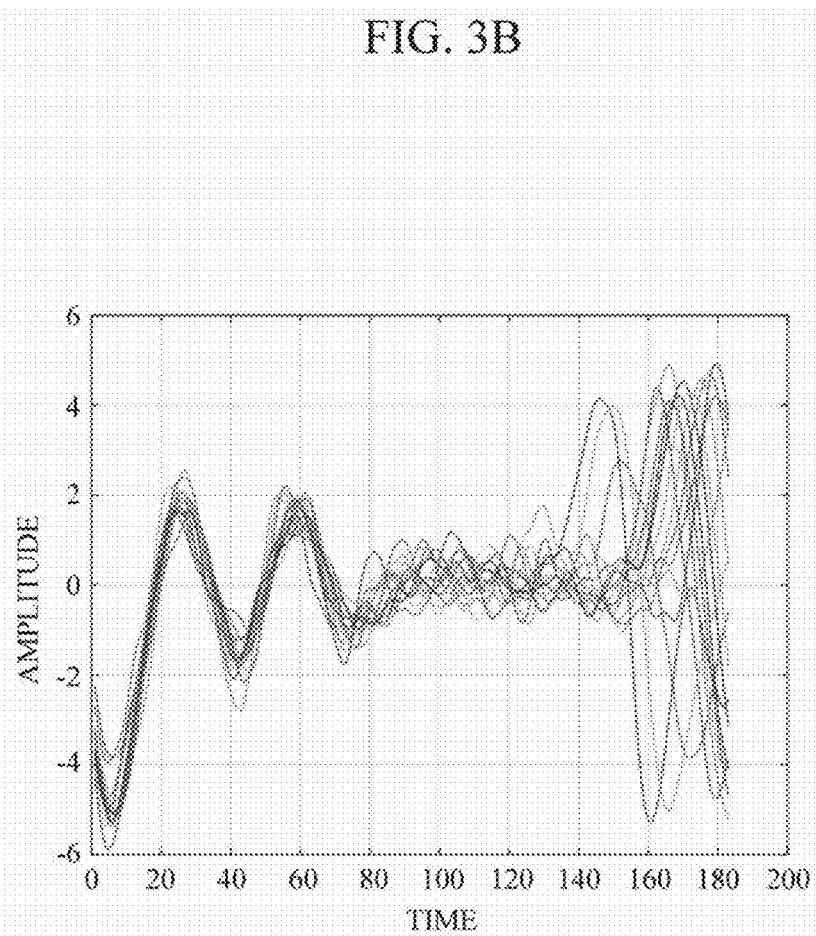

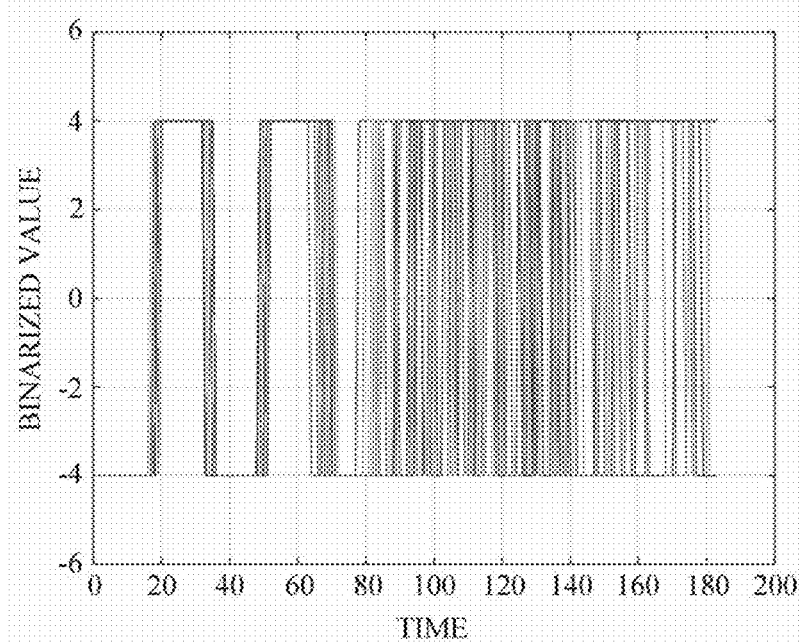

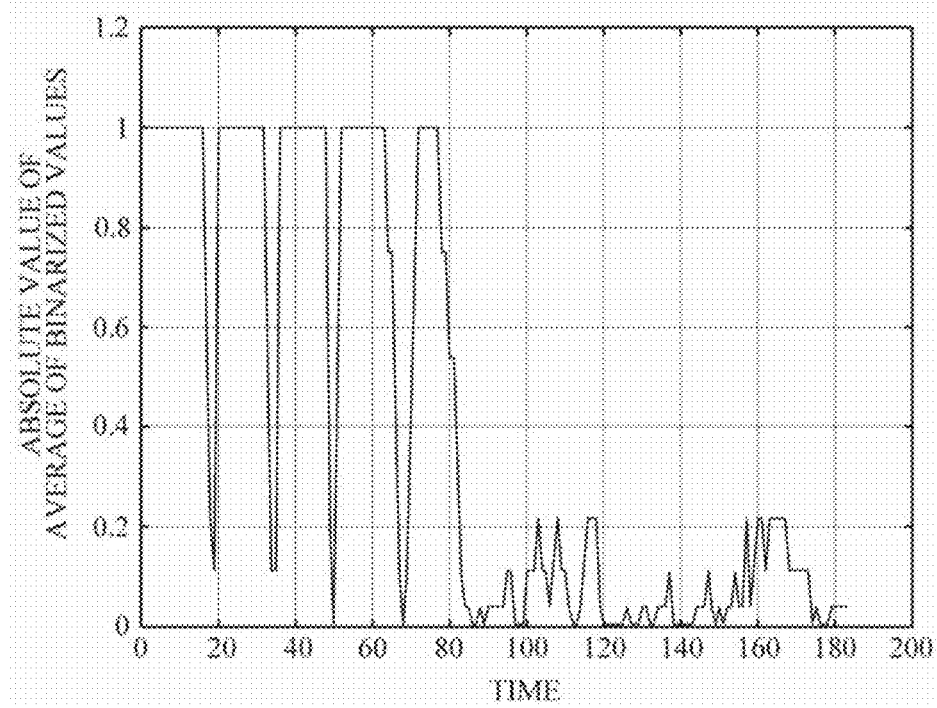

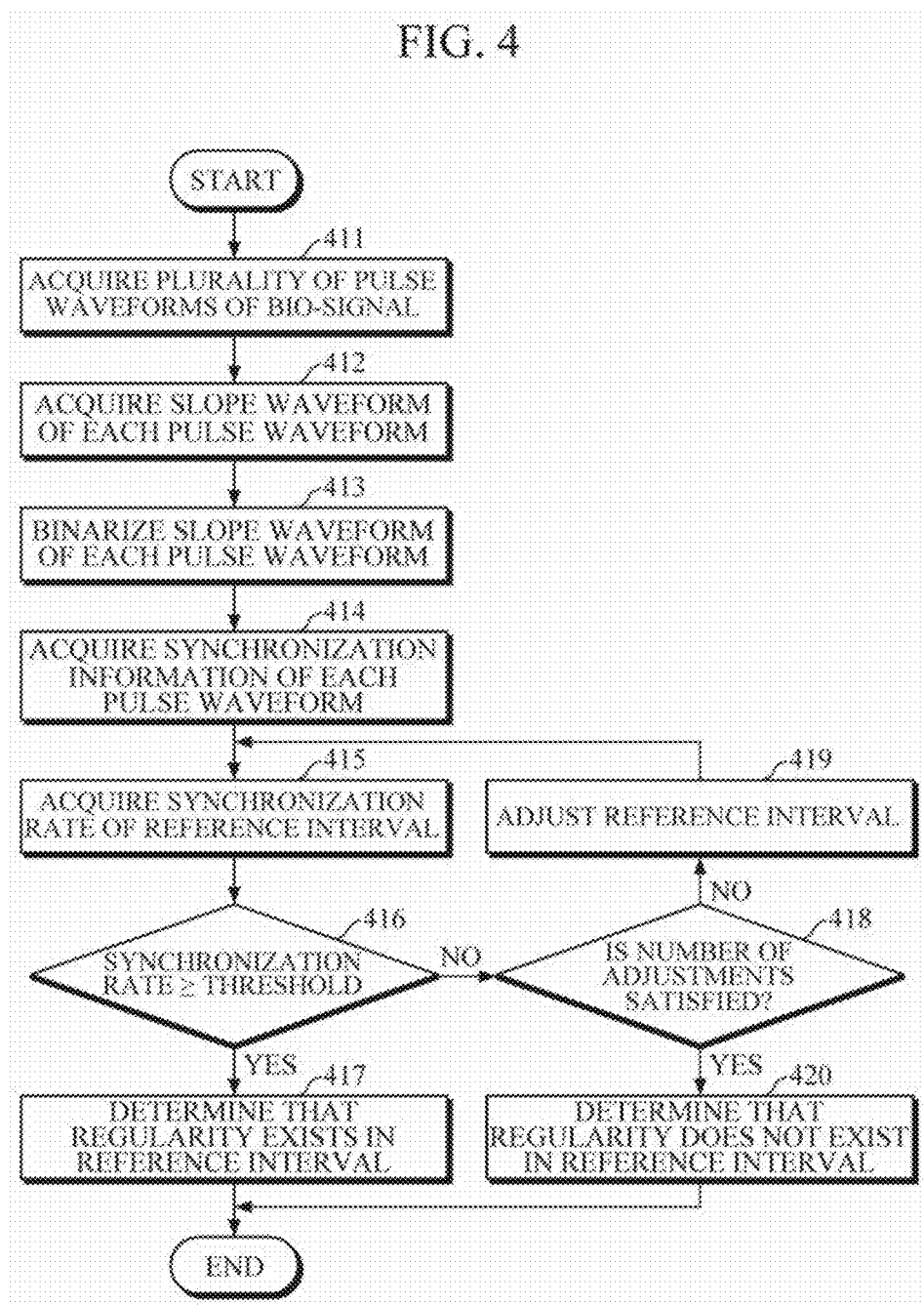

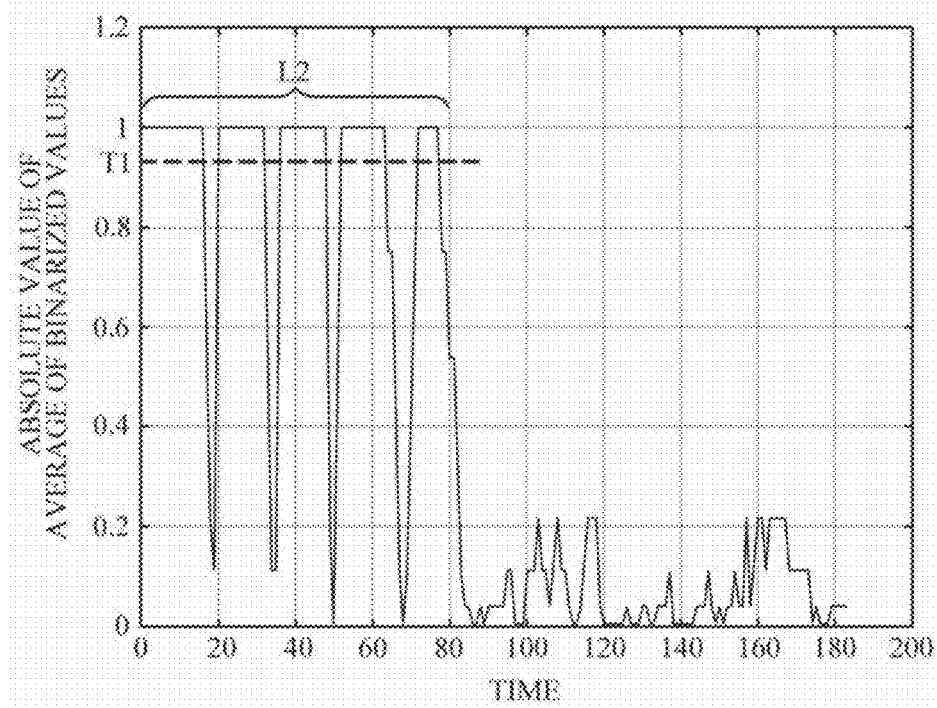

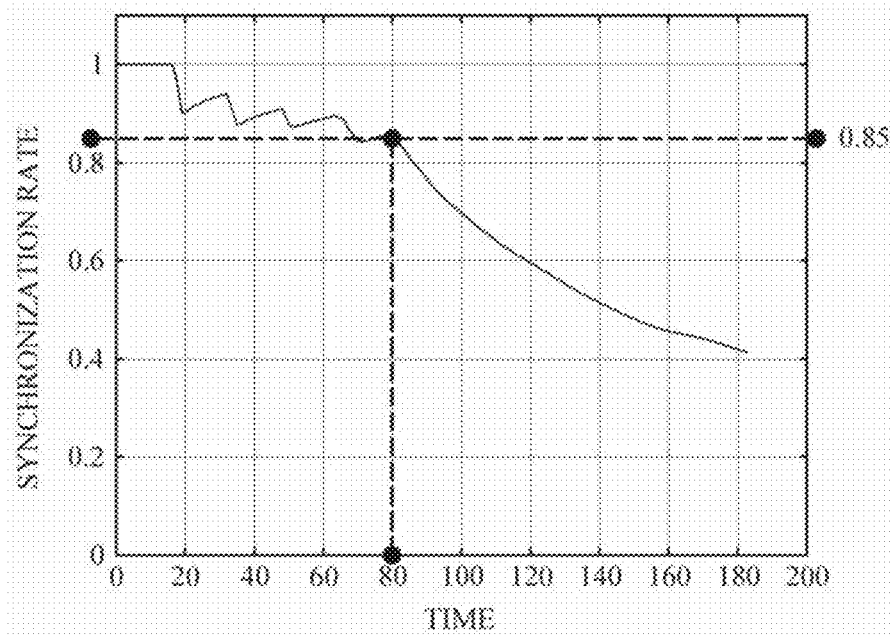

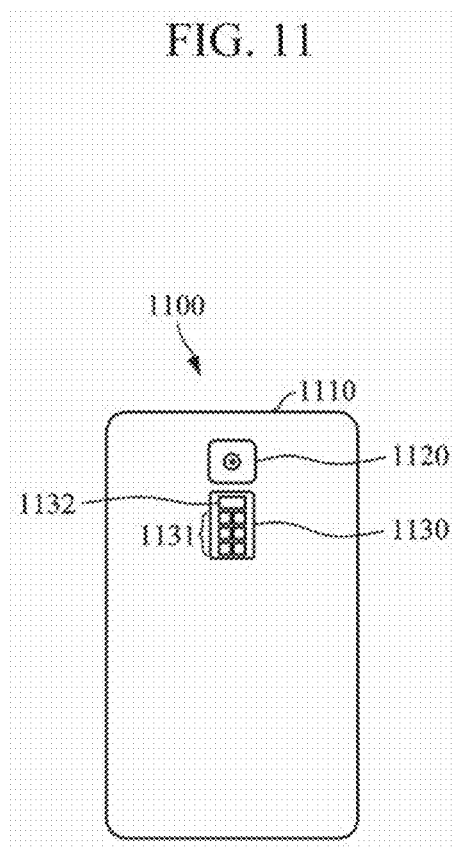

METHOD OF DETERMINING REGULARITY OF BIO-SIGNAL, APPARATUS AND METHOD FOR ESTIMATING BIO-INFORMATION

CROSS-REFERENCE TO RELATED APPLICATION(S)

This application claims priority to Korean Patent Application No. 10-2020-0116088, filed on Sep. 10, 2020, in the Korean Intellectual Property Office, the disclosure of which is incorporated by reference herein in its entirety.

BACKGROUND

1. Field

Example embodiments of the present disclosure relate to a method of determining regularity of a bio-signal, and a technique for estimating bio-information through determination of the regularity of a bio-signal.

2. Description of Related Art

With the aging population, increased medical costs, and a lack of medical personnel for specialized medical services, research is being actively conducted on information technology (IT)-medical convergence technologies, in which IT and medical technology are combined. In particular, health monitoring systems have extended care from hospitals to patients' homes and offices so that the patients can monitor their health state in daily life. Some examples of bio-signals, which indicate the health condition of individuals, may include an electrocardiography (ECG) signal, a photoplethysmogram (PPG) signal, an electromyography (EMG) signal, and the like, and various bio-signal sensors are being developed to measure the bio-signals in daily life. For example, the PPG sensor may estimate blood pressure of a human body by analyzing a pulse waveform which reflects a condition of the cardiovascular system, and the like.

According to the PPG bio-signal-related research, a waveform of a PPG signal may be a summation of a propagation wave propagating from the heart to peripheral parts of a body and reflection waves returning from the peripheral parts of the body. In addition, it is known that information for use in estimating blood pressure can be obtained by extracting various features related to the propagation wave or the reflection waves. However, if the quality of the bio-signal is degraded due to arrhythmia or motion noise of the heartbeat, the accuracy of blood pressure estimation may decrease.

SUMMARY

According to an aspect of an example embodiment, a method of determining regularity of a bio-signal may include acquiring a plurality of pulse waveforms of the bio-signal; acquiring a plurality of slope waveforms corresponding to the plurality of pulse waveforms; binarizing the plurality of slope waveforms; acquiring synchronization information of the plurality of pulse waveforms based on binarizing the plurality of pulse waveforms; acquiring a synchronization rate of a reference interval based on the synchronization information; and determining whether the bio-signal is regular or irregular based on the synchronization rate of the reference interval.

The bio-signal may include at least one of an electrocardiography (ECG) signal, a photoplethysmogram (PPG) signal, a ballistocardiogram (BCG) signal, an electromyography (EMG) signal, an impedance plethysmogram (IPG) signal, a pressure wave signal, or a video plethysmogram (VPG) signal.

The acquiring of the plurality of slope waveforms may include acquiring the plurality of slope waveforms by differentiating the plurality of pulse waveforms.

The binarizing of the plurality of slope waveforms may include binarizing the plurality of slope waveforms to a first value based on a slope value at each point in time being a positive number, and binarizing the plurality of slope waveforms to a second value based on the slope value at each point in time being a negative number.

The acquiring of the synchronization information may include acquiring absolute values of averages of values binarized at each point in time as the synchronization information.

The determining whether the bio-signal is regular or irregular may include determining that the bio-signal is regular based on the synchronization rate of the reference interval being greater than or equal to a predetermined threshold.

The method may include, based on the synchronization rate of the reference interval being less than a predetermined threshold, adjusting the reference interval; and acquiring another synchronization rate based on adjusting the reference interval.

The adjusting the reference interval may include adjusting the reference interval so that a predetermined number of peak points are included in the reference interval based on the synchronization information.

The method may include setting the reference interval based on the synchronization information or a value acquired based on at least one of a type of a bio-signal, a type of bio-information to be estimated, or a user's characteristic information.

According to an aspect of an example embodiment, an apparatus for estimating bio-information may include a sensor configured to measure a bio-signal from an object; and a processor configured to acquire synchronization information of a plurality of pulse waveforms constituting the bio-signal based on a plurality of slope waveforms corresponding to the plurality of pulse waveforms; acquire a synchronization rate of a reference interval based on the acquired synchronization information; determine whether the bio-signal is regular or irregular based on the synchronization rate of the reference interval; and estimate the bio-information using the bio-signal based on the bio-signal being regular.

The processor may acquire the plurality of slope waveforms corresponding to the plurality of pulse waveforms by differentiating the plurality of pulse waveforms of the bio-signal.

The processor may binarize the slope waveform to a first value based on a slope value at each point in time being a positive number, and binarize the slope waveform to a second value based on the slope value at each point in time being a negative number.

The processor may acquire absolute values of averages of the values binarized at each point in time as the synchronization information.

The processor may acquire an average of the absolute values in the reference interval among the acquired absolute values as the synchronization rate of the reference interval.

The processor may determine that the bio-signal is regular based on the synchronization rate of the reference interval being greater than or equal to a predetermined threshold.

The processor may, based on the synchronization rate of the reference interval being less than a predetermined threshold, adjust the reference interval; and acquire a synchronization rate.

The processor may determine a representative pulse waveform from among the plurality of pulse waveforms based on the bio-signal being regular; and extract a feature to be used for bio-information estimation from the determined representative pulse waveform.

The processor may extract the feature by searching an interval of the representative pulse waveform that corresponds to the reference interval.

The processor may detect one or more minimum points from the representative pulse waveform; and extract at least one of a time and an amplitude of the bio-signal that corresponds to the detected minimum points as the feature.

The processor may, based on the bio-signal being irregular, control an output interface to guide re-measurement of the bio-signal, or terminate bio-signal estimation.

The processor may, based on the bio-signal that is measured for a first period of time being irregular, control the sensor to increase a measurement time and measure the bio-signal for a second period of time; and determine whether the bio-signal that is measured for the second period is regular or irregular.

The bio-information may include one or more of a blood pressure, a cardiac arrhythmia, a vascular age, skin elasticity, a skin age, an arterial stiffness, an aortic pressure waveform, a stress index, and a degree of fatigue.

According to an aspect of an example embodiment, a method of estimating bio-information may include measuring a bio-signal from an object; decomposing the bio-signal into a plurality of pulse waveforms; acquiring synchronization information of the plurality of pulse waveforms based on a plurality of slope waveforms corresponding to the plurality of pulse waveforms; acquiring a synchronization rate of a reference interval based on the synchronization information; determining whether the bio-signal is regular or irregular based on the synchronization rate of the reference interval; and estimating the bio-information using the bio-signal based on determining that the bio-signal is regular.

The method may include binarizing the plurality of slope waveforms at each point in time of the reference interval.

The acquiring of the synchronization information may include acquiring absolute values of averages of the values binarized at each point in time as the synchronization information.

The acquiring of the synchronization rate of the reference interval may include acquiring an average of the absolute values in the reference interval among the acquired absolute values as the synchronization rate of the reference interval.

The estimating of the bio-information may include determining a representative pulse waveform from among the plurality of pulse waveforms based on the bio-signal being regular and extracting a feature to be used for bio-information estimation from the determined representative pulse waveform.

The extracting of the feature may include extracting the feature by searching an interval of the representative pulse waveform that corresponds to the reference interval.

The method may include, based on determining that the bio-signal is regular, at least one of increasing a bio-signal measurement time; guiding re-measurement of the bio-signal, or terminating of bio-information estimation.

Other features and aspects will be apparent from the following detailed description, the drawings, and the claims.

BRIEF DESCRIPTION OF THE DRAWINGS

The above and other aspects will be more apparent from the following description of example embodiments taken in conjunction with the accompanying drawings, in which:

FIG. 2 is a flowchart illustrating a method of determining regularity of a bio-signal according to an example embodiment;

FIGS. 3A to 3F are graphs for describing each operation of determining regularity of a bio-signal;

FIG. 4 is a flowchart illustrating a method of determining regularity of a bio-signal according to another example embodiment;

FIGS. 5A and 5B are graphs for describing a method of adjusting a reference interval;

FIG. 11 is a block diagram illustrating a smart device according to another example embodiment.

Figure 1:
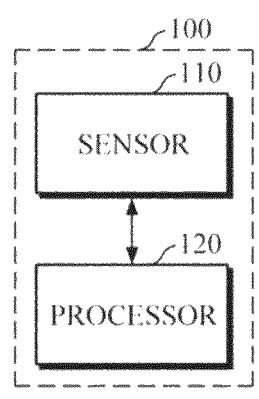
FIG. 1 is a block diagram illustrating an apparatus for determining regularity of a bio-signal according to an example embodiment.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

DETAILED DESCRIPTION

Details of example embodiments are provided in the following detailed description with reference to the accompanying drawings. The disclosure may be understood more readily by reference to the following detailed description of example embodiments and the accompanying drawings. The disclosure may, however, be embodied in many different forms and should not be construed as being limited to the example embodiments set forth herein. Rather, these example embodiments are provided so that the disclosure will be thorough and complete and will fully convey the concept of the present disclosure to those skilled in the art, and the disclosure will only be defined by the appended claims. Like reference numerals refer to like elements throughout the specification.

It will be understood that, although the terms "first," "second," etc. may be used herein to describe various elements, these elements should not be limited by these terms. These terms are only used to distinguish one element from another. Also, the singular forms of terms are intended to include the plural forms of the terms as well, unless the context clearly indicates otherwise. In the specification, unless explicitly described to the contrary, the word "comprise," and variations such as "comprises" or "comprising,"

will be understood to imply the inclusion of stated elements but not the exclusion of any other elements. Terms such as "unit" and "module" denote units that process at least one function or operation, and the units may be implemented by using hardware, software, or a combination of hardware and software.

FIG. 1 is a block diagram illustrating an apparatus for determining regularity of a bio-signal according to an example embodiment.

Referring to FIG. 1, an apparatus 100 for determining regularity of a bio-signal includes a sensor 110 and a processor 120.

The sensor 110 may acquire a bio-signal for regularity determination. In this case, the bio-signal may be a bio-signal that is continuously measured for a predetermined period of time and exhibits a plurality of repeated pulse waveforms. However, the bio-signal does not necessarily have to be a bio-signal that is continuously acquired for a predetermined period of time, and may be a plurality of bio-signals having single pulse waveforms measured at different points in time. Also, the bio-signals do not need to be bio-signals of the same kind. The bio-signal may include an ECG signal, a PPG signal, a ballistocardiogram (BCG) signal, an EMG signal, an impedance plethysmogram (IPG) signal, a pressure wave signal, and a video plethysmogram (VPG) signal, but is not limited thereto. In addition, the bio-signals to be subjected to a regularity determination process may include various signals measured from a body part of a user, or may include signals obtained by differentiating the measured signals, such as second-order differential signals.

For example, the sensor 110 may include various sensors that measure the aforementioned bio-signals. The sensor 110 may measure bio-signals from various body parts of the user. The sensor 110 may transmit the measured bio-signal or a bio-signal obtained by, for example, second-order differentiation of the measured bio-signal to the processor 120.

For example, the sensor 110 may include a PPG sensor. The PPG sensor may include one or more light sources configured to emit light to the user's body part, and one or more detectors configured to detect light reflected or scattered from the body part. The light source may include a light emitting diode (LED), a laser diode, a phosphor, and the like. The light source may be formed as a single light source or an array of two or more light sources. Each light source may emit light of different wavelengths. In addition, the detector may include a photodiode, a phototransistor, a complementary metal-oxide semiconductor (CMOS) image sensor, a charge-coupled device (CCD) image sensor, and the like, and may be formed as a single detector or an array of two or more detectors.

In another example, the sensor 110 may receive a bio-signal from an external device by using wired or wireless communication techniques. The external device may include a smart device or a wearable device which is equipped with a bio-signal measurement sensor or a bio-signal measurement function. The wired or wireless communication techniques may include, but are not limited to, Bluetooth communication, Bluetooth low energy (BLE) communication, near field communication (NFC), wireless local access network (WLAN) communication, ZigBee communication, infrared data association (IrDA) communication, wireless fidelity (Wi-Fi) Direct (WFD) communication, ultra-wideband (UWB) communication, Ant+ communication, Wi-Fi communication, radio frequency identification (RFID) communication, third generation (3G) communication, fourth generation (4G) communication, and/or fifth generation (5G) communication.

The processor 120 may be electrically connected to the sensor 110 to control the sensor 110. Based on receiving the bio-signal from the sensor 110, the processor 120 may determine regularity of the bio-signal. The processor 120 may determine the regularity based on the slope of the bio-signal. The processor 120 may determine the regularity of the bio-signal so that various features to be used for bio-information estimation can be extracted from the bio-signal. The processor 120 may extract an interval during which the corresponding signal increases or decreases from a slope waveform of the bio-signal, and may determine whether regularity exists in this interval.

Hereinafter, various example embodiments of a method of determining regularity of a bio-signal will be described with reference to FIGS. 2 to 5B.

FIG. 2 is a flowchart illustrating a method of determining regularity of a bio-signal according to an example embodiment. FIGS. 3A to 3F are graphs for describing each operation of determining regularity of a bio-signal.

Referring to FIG. 2, the apparatus 100 for determining regularity of a bio-signal may acquire a plurality of pulse waveforms from a bio-signal to be analyzed for regularity (operation 211). For example, the bio-signal may be filtered and decomposed into a plurality of pulse waveforms. For example, a waveform of the bio-signal may be ensemble averaged in units of a predetermined number of bits to acquire a plurality of pulse waveforms, or a waveform of the bio-signal may be decomposed into a plurality of waveforms by gating based on a feature point of a reference signal such as, for example, an R-wave of an ECG signal. However, these are merely examples. FIG. 3A shows 15 pulse waveforms superimposed on one another. Here, the pulse waveforms are superimposed based on a predefined reference point. For example, the reference point may be a starting point of each pulse waveform. However, embodiment are not limited thereto.

Based on acquiring the plurality of pulse waveforms, the apparatus 100 may acquire a slope waveform of each pulse waveform (operation 212). For example, the apparatus 100 for determining regularity may acquire a slope waveform by differentiating each pulse waveform. FIG. 3B shows slope waveforms superimposed on one another, which are obtained by differentiating the 15 pulse waveforms.

Based on acquiring the slope waveforms, the apparatus 100 may binarize each of the slope waveforms in order to extract increase and decrease information of the pulse waveform (operation 213). For example, regardless of a slope value at each point in time, the slope waveform is binarized to +1 based on a slope value being a positive number, and is binarized to −1 based on a slope value being a negative number. For example, in FIG. 3B, because slope values of all pulse waveforms in the interval between time index 0 through 18 are smaller than 0, the waveforms are all converted into −1. Also, because slope values of some pulse waveforms in the interval between time index 18 and 20 are smaller than 0, the pulse waveforms are converted into −1. Further, because the remaining pulse waveforms have slope values greater than 0, the remaining slope waveforms are converted into +1. FIG. 3C shows the binarized values of each pulse waveform obtained in this way at each point in time.

Based on binarizing the slope waveforms, the apparatus 100 may acquire synchronization information of each pulse waveform based on the binarization result of each superimposed pulse waveform (operation 214). For example, all the binarized values at a specific point in time may be added and divided by the number of pulse waveforms to obtain the average, and then the absolute value of the average may be obtained to acquire synchronization information. In this way, the absolute values of the averages at all points in time may be obtained. Based on all pulse waveforms increasing or decreasing in the same direction, the absolute value of the average is 1. In this case, in order to apply more weighting to the case where all pulse waves increase or decrease in the same direction, such as where the absolute value of the average is 1, the absolute values of the averages acquired at each point in time may be raised to the $M^{th}$ power. In this case, M may be an integer that is greater than or equal to 2. FIG. 3D shows synchronization information obtained by raising the absolute value of the average of binarized values at each point in time to the second power.

Based on acquiring the synchronization information, the apparatus 100 may acquire an average synchronization rate of a reference interval using the absolute value of the average at each point in time (operation 215). For example, referring to FIG. 3E, an average synchronization rate of a reference interval L1 may be acquired by averaging the absolute values of the averages in the reference interval L1. In this case, the reference interval may be set to a value that is obtained in advance through preprocessing based on the type of a bio-signal, the type of bio-information to be estimated, characteristic information of a user, and the like. Alternatively, the apparatus 100 for determining regularity may set the reference interval by using the absolute value of the average at each point in time before acquiring the average synchronization rate. For example, as will be described below, the reference interval may be set to include a preset number of peak points based on the absolute value of the average.

Figure 3E:
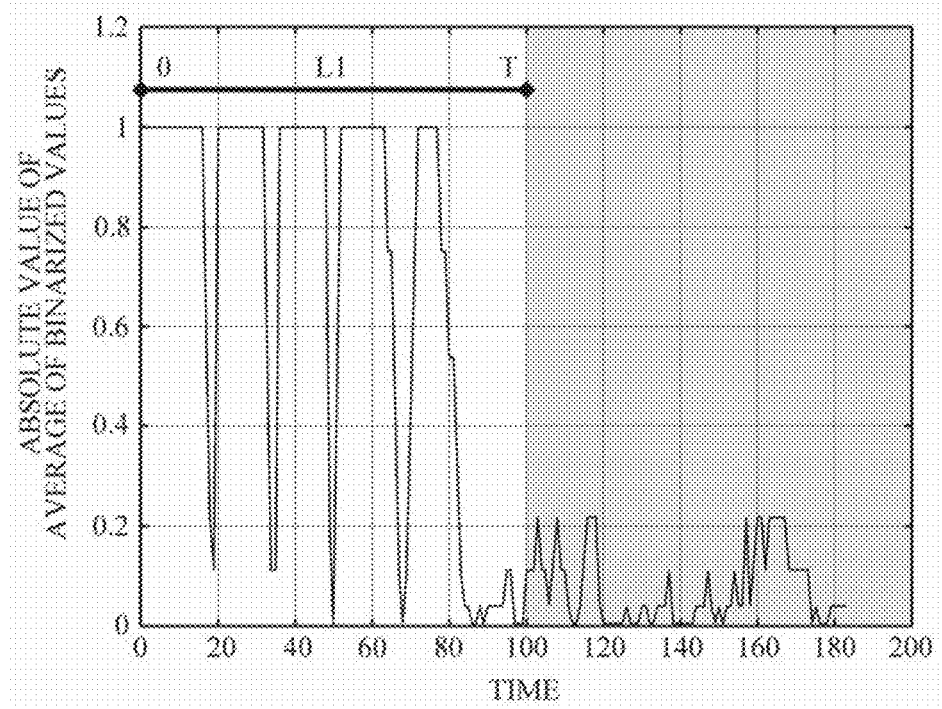
Figure 3F:
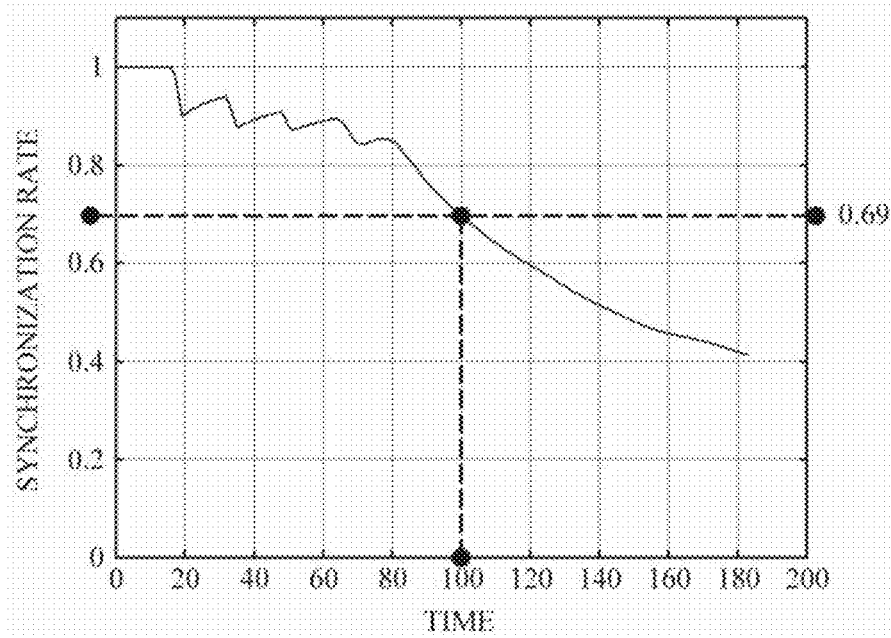

Based on acquiring the synchronization rate, the apparatus 100 may determine whether the average synchronization rate of the reference interval is greater than or equal to a preset threshold (operation 216). Based on the average synchronization rate of the reference interval being greater than or equal to the preset threshold (operation 216—YES), the apparatus 100 may determine that regularity exists in the reference interval (operation 217). In other words, the apparatus 100 may determine that the bio-signal is regular. Alternatively, based on the average synchronization rate of the reference interval being less than the preset threshold (operation 216—NO), the apparatus 100 may determine that regularity does not exist in the reference interval (operation 218). In other words, the apparatus 100 may determine that the bio-signal is irregular. For example, FIG. 3F is a graph showing the average synchronization rate of an interval from a starting point 0 to each time index, which is obtained by gradually increasing the time index. Referring to FIG. 3F, the average synchronization rate of the reference interval (0-100) set in FIG. 3E is 0.69. Based on the average synchronization rate of 0.69 of the reference interval (0-100) being greater than or equal to a threshold, it may be determined that regularity exists in the reference interval, and otherwise, it may be determined that regularity does not exist in the reference interval (0-100).

FIG. 4 is a flowchart illustrating a method of determining regularity of a bio-signal according to another example embodiment. FIGS. 5A and 5B are graphs for describing a method of adjusting a reference interval.

Referring to FIG. 4, the apparatus 100 for determining regularity of a bio-signal may acquire a plurality of pulse waveforms of a bio-signal to be analyzed for regularity (operation 411).

Based on acquiring the plurality of pulse waveforms, the apparatus 100 may differentiate each pulse waveform to obtain a slope waveform thereof (operation 412).

Based on acquiring the slope waveforms, the apparatus 100 may binarize each slope waveform in order to extract increase and decrease information of the corresponding pulse waveform (operation 413).

Based on binarizing the slope waveforms, the apparatus 100 may acquire synchronization information of each pulse waveform based on the binarization result of each superimposed pulse waveform (operation 414). For example, the binarized values at each point in time may be added and divided by the number of pulse waveforms to obtain the average, and then the absolute value of the average may be obtained.

Based on acquiring the synchronization information, the apparatus 100 may acquire an average synchronization rate of a first reference interval using the absolute value of the average at each point in time (operation 415). Initially, the first reference interval may be set by using a value obtained in advance through preprocessing based on the type of bio-signal, the type of bio-information to be estimated, the user's characteristic information, and/or the absolute value of the average at each point in time obtained in operation 414.

Based on acquiring the average synchronization rate, the apparatus 100 may determine whether the average synchronization rate is greater than or equal to a preset threshold (operation 416). Based on the average synchronization rate of the first reference interval being greater than or equal to the preset threshold (operation 416—YES), the apparatus 100 may determine that regularity exists in the first reference interval (operation 417). In other words, the apparatus 100 may determine that the bio-signal is regular.

Alternatively, based on the average synchronization rate being less than the preset threshold (operation 416—NO), the apparatus 100 may determine whether the number of adjustments of the reference interval is satisfied (operation 418). Based on determining that the number of adjustments of the reference interval is not satisfied (operation 418—NO), the apparatus 100 may adjust the first reference interval to a second reference interval (operation 419). In this case, the number of adjustments may be preset.

For example, assuming that the first reference interval is from 0 to 100 and the average synchronization rate of the first reference interval (0-100) is 0.69 as shown in FIG. 3F, the apparatus 100 may determine that regularity does not exist in the first reference interval (0-100) based on the preset threshold being 0.8. The apparatus 100 for determining regularity may set an interval from time interval 0 to 80 to be the second reference interval L2 by adjusting the reference interval so that the absolute values of the averages acquired in operation 414 are greater than or equal to a preset threshold T1 as shown in FIG. 5A. For example, the apparatus 100 for determining regularity may set the second reference interval to be the interval (0-80) in which the number of peak points, at each of which the absolute value of the average acquired in operation 414 is greater than or equal to the threshold T1, satisfies a preset number (e.g., 5).

Based on the second reference interval being set, the apparatus 100 may acquire an average synchronization rate of the second reference interval (operation 415), and based on the average synchronization rate of the second reference interval being greater than or equal to a threshold (operation 416—YES), the apparatus 100 may determine that regularity exists in the second reference interval (operation 417). In other words, the apparatus 100 may determine that the bio-signal is regular. Alternatively, based on the average synchronization rate of the second reference interval being less than the threshold (operation 416—NO), the apparatus 100 may determine whether the number of adjustments is satisfied (operation 418), and based on the number of adjustments being satisfied (operation 418—YES), the apparatus 100 may refrain from adjusting the reference interval, and may determine that regularity does not exist in the second reference interval. In other words, the apparatus 100 may determine that the bio-signal is irregular. Referring to FIG. 5B, based on the average synchronization rate of the second reference interval 0-80 being 0.85 and the threshold being 0.8 as described above, the apparatus 100 may determine that the bio-signal has regularity in the second reference interval.

Figure 6:
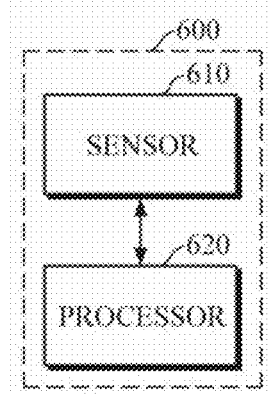
FIG. 6 is a block diagram illustrating an apparatus for estimating bio-information according to an example embodiment.

FIG. 6 is a block diagram illustrating an apparatus for estimating bio-information according to an example embodiment.

Referring to FIG. 6, an apparatus 600 for estimating bio-information includes a sensor 610 and a processor 620.

The sensor 610 may measure a bio-signal from a user. For example, the sensor 610 may include a light source and a detector, and measure a PPG signal from a body part using the light source and the detector based on the sensor being in contact with the body part of the user and hence a contact pressure changes. However, the bio-signal is not limited to a PPG signal and may include an ECG signal, a BCG signal, an IPG signal, a VPG signal, and the like.

The processor 620 may receive the bio-signal from the sensor 610 and estimate bio-information using the received bio-signal. In this case, the bio-information includes, but is not limited to, a blood pressure, a cardiac arrhythmia, a vascular age, skin elasticity, a skin age, an arterial stiffness, an aortic pressure waveform, a stress index, and a degree of fatigue.

The processor 620 may remove noise, such as motion noise, by using various noise removal techniques, such as filtering or smoothing of a bio-signal. For example, based on the bio-signal being a PPG signal, a bandpass filtering with cut-off frequencies of 1 Hz to 10 Hz may be performed.

The processor 620 may acquire the bio-signal and acquire a plurality of pulse waveforms by dividing the waveforms of the bio-signal. Also, the processor 620 may determine the regularity of the bio-signal based on the plurality of acquired pulse waveforms. The process of determining the regularity of the bio-signal is described above, and hence it will be briefly described below.

For example, the processor 620 may acquire slope waveforms by differentiating each of the pulse waveforms and determine the regularity based on the slope waveforms of each of the pulse waveforms. The processor 620 may binarize each slope waveform in order to extract increase and decrease information of the pulse waveform, add all the binarized values at each point in time and then divide the sum by the number of pulse waveforms to acquire an average, and obtain the absolute value of the average to acquire synchronization information of the pulse waveforms. At this time, regardless of a slope value at each point in time, the slope waveform is binarized to +1 based on a slope value being a positive number, and is binarized to −1 based on a slope value being a negative number. In addition, an average synchronization rate of a reference interval may be acquired using the absolute value of the average at each point in time.

Based on the average synchronization rate of the reference interval acquired as described above being greater than or equal to a predetermined threshold, the processor 620 may determine that the bio-signal has regularity in the reference interval, and may estimate bio-information using the bio-signal.

Based on the bio-signal having regularity, the processor 620 may extract one or more features to be used for bio-information estimation. The processor 620 may determine one of the plurality of pulse waveforms as a representative waveform and extract the features by searching a reference interval of the determined representative waveform. For example, one pulse waveform, for example, the first pulse waveform, may be determined as a representative waveform based on a time index at which the bio-signal is measured. However, embodiments are not limited thereto. Also, two or more pulse waveforms may be determined as representative waveforms, and based on there being two or more representative waveforms, features may be extracted from each pulse waveform.

For example, the processor 620 may extract amplitudes and/or times of component pulse waveforms constituting the bio-signal, such as component pulse waveforms related to a propagation wave and a reflection wave, as features. In this case, a reference interval of the bio-signal determined to have regularity is searched to extract a time at a minimum point, and the processor 620 may extract the amplitude of the bio-signal that corresponds to the extracted time at the minimum point as a feature. However, embodiments are not limited thereto, and a shape of the waveform of the bio-signal, time and/or amplitude at a maximum point in a systolic interval of the bio-signal, time and/or amplitude at a minimum point of the bio-signal, the entire or partial area of the bio-signal waveform, or time lapse of the bio-signal may be extracted as a feature.

The processor 620 may combine one or more of the acquired features and estimate bio-information by using a predefined bio-information estimation model. The bio-information estimation model may be predefined using various techniques, such as a linear function equation, nonlinear regression analysis, a neural network, deep learning, and the like.

Based on determining that the bio-signal does not have regularity in the reference interval, the processor 620 may control an output interface to guide the user to re-measure the bio-signal, or terminate the bio-information estimation.

Based on the sensor 610 measuring a bio-signal for a first period of time (e.g., 40 seconds), the processor 620 may determine the regularity of the measured bio-signal. If the measured bio-signal does not have regularity, the processor 620 may control the sensor 610 to increase a measurement time and further measure the bio-signal for a second period of time (e.g., 20 seconds) consecutively following the first period of time. The processor 620 may re-determine the regularity based on the bio-signal measured for the first period of time and the second period of time.

Also, the processor 620 may determine whether there is a risk of arrhythmia based on the regularity determination result of the bio-signal. For example, the processor 620 may determine the number of times that a reference interval is determined to be irregular as compared to the total number of times that the regularity of the reference interval is determined for a predetermined period of time, and determine an interval that has regularity each time the regularity is determined. Based on a preset criterion being satisfied, such as a case in which a rate of change of the interval having regularity is greater than or equal to a threshold, or a case in which irregularity is constantly repeated during a certain period of the day, for example, during the night sleep period, the processor 620 may determine that there is a risk of arrhythmia.

Figure 7:
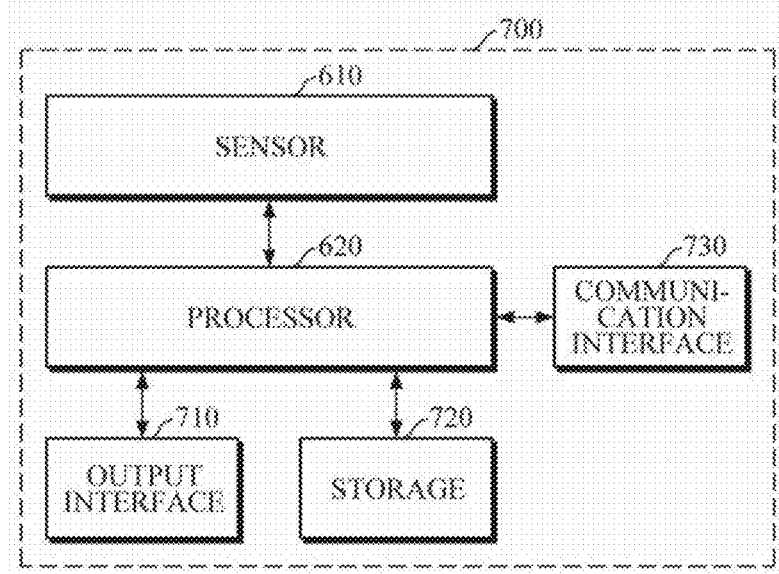
FIG. 7 is a block diagram illustrating an apparatus for estimating bio-information according to another example embodiment.

FIG. 7 is a block diagram illustrating an apparatus for estimating bio-information according to another example embodiment.

Referring to FIG. 7, an apparatus 700 for estimating bio-information may include a sensor 610, a processor 620, an output interface 710, a storage 720, and a communication interface 730. The configuration of the sensor 610 and the processor 620 is described in the example embodiment of FIG. 6.

The output interface 710 may provide a processing result of the processor 620 to a user. For example, the output interface 710 may include a display that may display a bio-information estimation value of the processor 620. In this case, if the bio-information estimation value is not within a normal range, warning information may be provided to the user by adjusting a color or a thickness of a line so that the user can easily recognize it or by displaying the normal range together. In addition, the output interface 710 may include a speaker or a haptic module that may provide the bio-information estimation value to the user in a non-visual manner, such as voice, vibration, and tactile sensation, together with or independently of a visual display.

Also, the output interface 710 may visually display a result of a regularity determination process performed by the processor 620 as a graph, or the like. In addition, based on determining that the bio-signal does not have regularity, the output interface 710 may guide the user to re-measure the bio-signal, or output information indicating that the bio-information estimation is terminated.

The storage 720 may store information related to bio-information estimation. For example, the storage 720 may store the bio-signal acquired by the sensor 610, a processing result of the processor 620 such as, for example, the result of determining regularity and the bio-information estimation value. In addition, the storage 720 may store a bio-information estimation model, a reference interval, the number of adjustments of a reference interval, a criterion for adjusting a reference interval, a threshold for determining regularity, user characteristic information, and the like. In this case, the user characteristic information may include the user's age, gender, health condition, or the like.

The storage 720 may include at least one type of storage medium, such as a flash memory type, a hard disk type, a multimedia card micro type, a card type memory (e.g., a secure digital (SD) or eXtreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disk, and the like, but is not limited thereto.

The communication interface 730 may communicate with an external device to transmit and receive various data related to the bio-information estimation. The external device may include an information processing device, such as a smartphone, a tablet personal computer (PC), a desktop computer, a laptop computer, and the like. For example, the bio-information estimation result may be transmitted to the external device, such as a user's smartphone, so that the user can manage and monitor a component analysis result through a device which has a relatively high performance.

The communication interface 730 may communicate with the external device by using various wired or wireless communication techniques. In this case, examples of the communication techniques may include Bluetooth communication, BLE communication, NFC, WLAN communication, ZigBee communication, IrDA communication, WFD communication, UWB communication, Ant+ communication, Wi-Fi communication, RFID communication, 3G communication, 4G communication, and/or 5G communication. However, is the foregoing techniques are merely examples and are not intended to be limiting.

Figure 8:
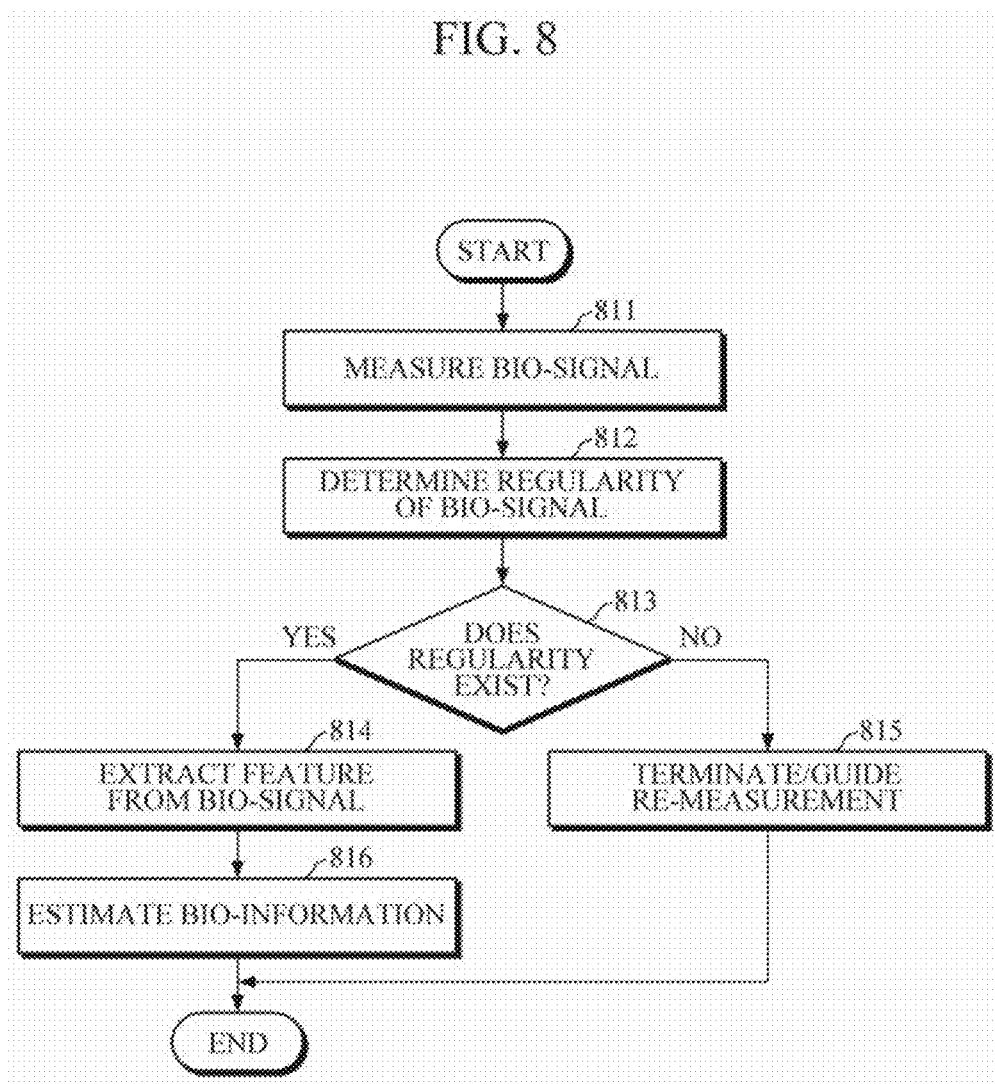
FIG. 8 is a flowchart illustrating a method of estimating bio-information according to an example embodiment.

FIG. 8 is a flowchart illustrating a method of estimating bio-information according to an example embodiment.

The method of FIG. 8 may correspond to a method performed by the apparatuses 600 or 700 for estimating bio-information according to the example embodiment of FIG. 6 or 7, which will be briefly described below to avoid redundancy.

Referring to FIG. 8, the apparatus for estimating bio-information may measure a bio-signal from a user through a sensor (operation 811), and determine regularity of the measured bio-signal (operation 812). In other words, the apparatus may determine whether the bio-signal is regular or irregular. The method of determining regularity of the bio-signal is described in detail above.

Based on determining that regularity exists (operation 813—YES), the apparatus may extract a feature from the bio-signal (operation 814), and estimate bio-information using the extracted feature (operation 816). For example, features related to a propagation waveform and a reflection waveform such as, for example, time and amplitude at a minimum point, may be extracted by searching a reference interval of the bio-signal that is determined to have regularity. Based on determining that regularity does not exist (operation 813—NO), the apparatus may terminate the bio-information estimation or control an output interface to guide the user to re-measure the bio-signal (operation 815).

Figure 9:
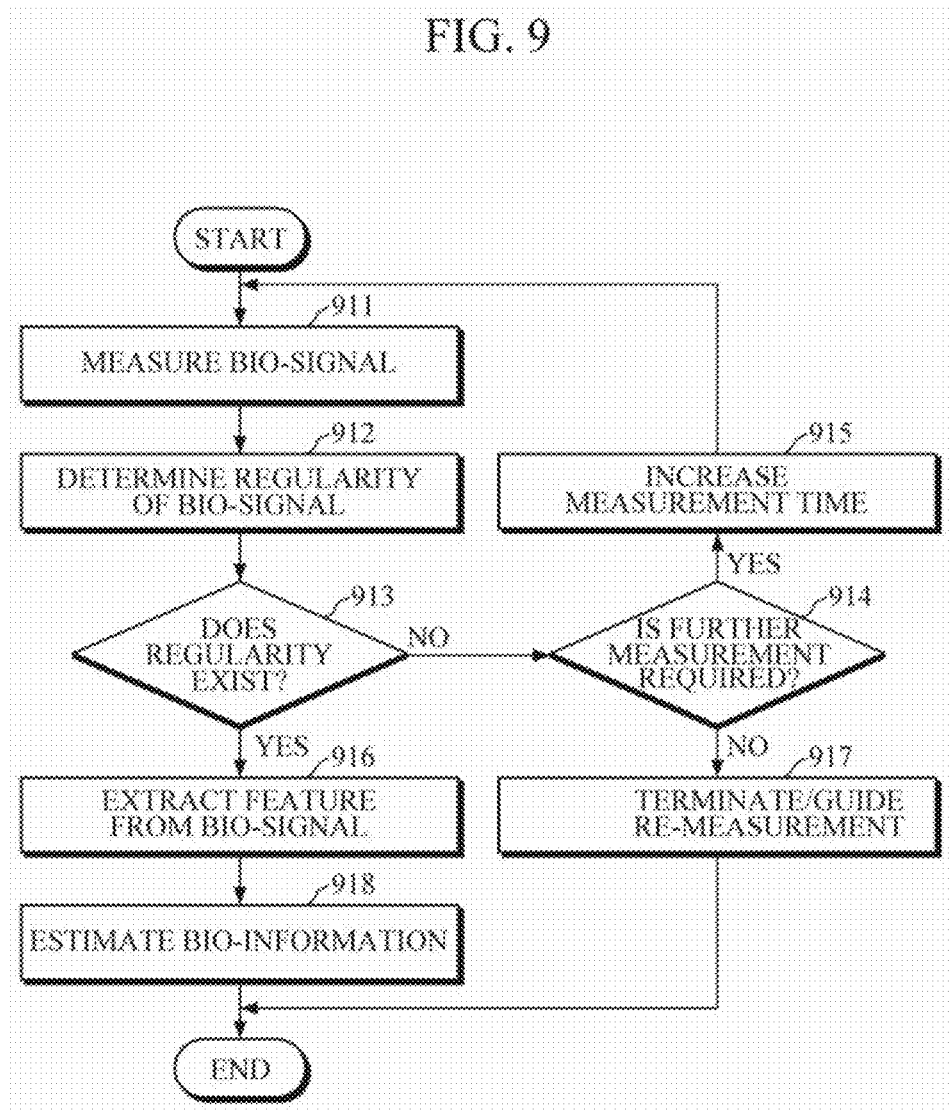
FIG. 9 is a flowchart illustrating a method of estimating bio-information according to another example embodiment.

FIG. 9 is a flowchart illustrating a method of estimating bio-information according to another example embodiment.

The method of FIG. 9 may correspond to a method performed by the apparatuses 600 or 700 for estimating bio-information according to the example embodiment of FIG. 6 or 7, which will be briefly described to avoid redundancy.

Referring to FIG. 9, the apparatus for estimating bio-information may measure a bio-signal from a user through a sensor (operation 911), and determine regularity of the measured bio-signal (operation 912). In other words, the apparatus may determine whether the bio-signal is regular or irregular. The method of determining regularity of the bio-signal is described in detail above.

Based on determining that regularity does not exist (operation 913—NO), the apparatus may determine whether further measurement is required (operation 914), and based on determining that the further measurement is required (operation 914—YES), the apparatus may increase the measurement time (operation 915), and the process returns to operation 911. Based on determining that the further measurement is not required (operation 914—NO), the apparatus may terminate the bio-information estimation or may control an output interface to guide the user for re-measurement (operation 917).

Based on determining that regularity exists (operation 913—YES), the apparatus may extract a feature from the bio-signal (operation 916), and estimate bio-information using the extracted feature (operation 918). In this case, the apparatus for estimating bio-information may extract features related to a propagation waveform and a reflection waveform such as, for example, time and amplitude at a minimum point, by searching a reference interval of the bio-signal that is determined to have regularity.

Figure 10:
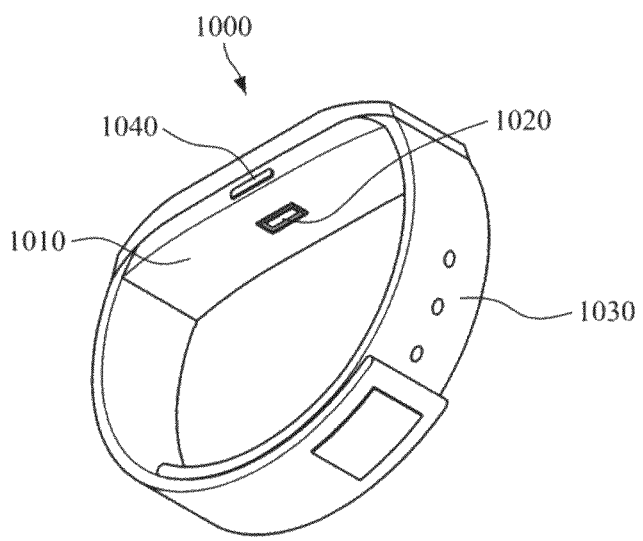
FIG. 10 is a block diagram illustrating a wearable device according to an example embodiment.

FIG. 10 illustrates a wearable device. The above-described example embodiments of the apparatuses 100, 600, and 700 for estimating bio-information may be embedded in the wearable device.

Referring to FIG. 10, the wearable device 1000 includes a main body 1010 and a strap 1030.

The strap 1030 may be connected to both ends of the main body 1010 and be made of a flexible material to conform to a user's wrist. The strap 1030 may include a first strap and a second strap that are separate from each other. Respective ends of the first strap and the second strap may be connected to respective ends of the main body 1010, and the first strap and the second strap may be fastened to each other via fastening means. In this case, the fastening means may be formed as a magnet fastening means, a Velcro fastening means, a pin fastening means, but is not limited thereto. In addition, the strap 1030 may be formed as an integrated piece, such as a band. In this case, air may be injected into the strap 1030 or an airbag may be included in the strap 1030, so that the strap 1030 may have elasticity according to a change in pressure applied to the wrist, and the change in pressure of the wrist may be transmitted to the main body 1010.

A battery, which supplies power to the wearable device 1000, may be embedded in the main body 1010 or the strap 1030.

A sensor 1020 is mounted on one side of the main body 1010. The sensor 1020 may include, for example, a light source and a detector.

A processor may be mounted inside the main body 1010 and be electrically connected to components of the wearable device 1000. The processor may control the sensor 1020, and based on receiving a bio-signal from the sensor 1020, may determine regularity of the bio-signal. Based on determining that the bio-signal has regularity, the processor may estimate bio-information based on the bio-signal.

In addition, a storage may be included inside the main body 1010 to store reference information for bio-information estimation and information processed by various components.

Also, a manipulator 1040 may be mounted on one side of the main body 1010 to receive a control command of the user and transmit the received control command to the processor. The manipulator 1040 may include a power button to input a command to turn on/off the wearable device 1000.

In addition, a display may be provided on the front surface of the main body 1010 to output information, and the display may include a touch screen capable of receiving touch input. The display may receive a user's touch input, transmit the received touch input to the processor, and display a processing result of the processor.

In addition, a communication interface that communicates with an external device may be mounted in the main body 1010. The communication interface may transmit a bio-information estimation result to the external device such as, for example, a user's smartphone.

FIG. 11 illustrates a smart device. The smart device may include a smartphone, a tablet PC, and the like. The smart device may include the functions of the apparatuses 100, 600, and 700 for estimating bio-information described above.

Referring to FIG. 11, a smart device 1100 may include a sensor 1130 mounted on one surface of a main body 1110. As illustrated, the sensor 1130 may include one or more light sources 1131 and one or more detectors 1132.

In addition, a display may be provided on the front surface of the main body 1110. The display may visually output a bio-information estimation result, a health condition evaluation result, and the like. The display may include a touch screen, receive information input through the touch screen, and transmit the received information to a processor.

The main body 1110 may include an image sensor 1120 as illustrated. The image sensor 1120 may perform a function of capturing various images, and for example, may acquire a fingerprint image of a finger when the finger contacts the sensor 1130.

The processor may be mounted in the main body 1110 and be electrically connected to various components to control the operation of the components. The processor may control the sensor 1130, and based on receiving a bio-signal from the sensor 1130, may determine regularity of the bio-signal. Based on determining that the bio-signal has regularity, the processor may estimate bio-information based on the bio-signal.

The example embodiments can be implemented by computer-readable code that is stored in a non-transitory computer-readable medium and that is executed by a processor. Code and code segments constituting the computer program can be inferred by a computer programmer skilled in the art. The computer-readable medium includes all types of recording media in which computer-readable data are stored. Examples of the computer-readable medium include a ROM, a RAM, a CD-ROM, a magnetic tape, a floppy disk, and an optical data storage. Further, the compute-readable medium may be implemented in the form of a carrier wave such as an Internet transmission. In addition, the computer-readable medium may be distributed to computer systems over a network, in which computer-readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating bio-information, the apparatus comprising:
   a sensor configured to measure a bio-signal from an object, the sensor comprising a light source and a single light detector which measures light reflected from the object;
   a display; and
   a processor configured to:
      acquire synchronization information of a plurality of pulse waveforms constituting the bio-signal based on a plurality of slope waveforms corresponding to the plurality of pulse waveforms as measured by the single light detector;
      acquire a synchronization rate of a reference interval based on the acquired synchronization information;

determine whether the bio-signal is regular or irregular based on the synchronization rate of the reference interval; and estimate the bio-information using the bio-signal based on determining that the bio-signal is regular, wherein the processor is further configured to, based on determining that the bio-signal is irregular, control the display to display the bio-signal determined to be irregular together with a regular bio-signal to guide a user to re-measure the bio-signal, wherein bio-signals from the single light detector are measured from a single point of contact with the object.

2. The apparatus of claim 1, wherein the processor is further configured to acquire the plurality of slope waveforms corresponding to the plurality of pulse waveforms by differentiating the plurality of pulse waveforms of the bio-signal.

3. The apparatus of claim 1, wherein the processor is further configured to binarize the slope waveform to a first value based on a slope value at each point in time being a positive number, and binarize the slope waveform to a second value based on the slope value at each point in time being a negative number.

4. The apparatus of claim 3, wherein the processor is further configured to acquire absolute values of averages of the values binarized at each point in time as the synchronization information.

5. The apparatus of claim 4, wherein the processor is further configured to acquire an average of the absolute values in the reference interval among the acquired absolute values as the synchronization rate of the reference interval.

6. The apparatus of claim 1, wherein the processor is further configured to determine that the bio-signal is regular based on the synchronization rate of the reference interval being greater than or equal to a predetermined threshold.

7. The apparatus of claim 1, wherein the processor is further configured to:
based on the synchronization rate of the reference interval being less than a predetermined threshold, adjust the reference interval; and
acquire a synchronization rate.

8. The apparatus of claim 1, wherein the processor is further configured to:
determine a representative pulse waveform from among the plurality of pulse waveforms based on determining that the bio-signal is regular; and
extract a feature to be used for bio-information estimation from the determined representative pulse waveform.

9. The apparatus of claim 8, wherein the processor is further configured to extract the feature by searching an interval of the representative pulse waveform that corresponds to the reference interval.

10. The apparatus of claim 8, wherein the processor is further configured to:
detect one or more minimum points from the representative pulse waveform; and
extract at least one of a time and an amplitude of the bio-signal that corresponds to the detected minimum points as the feature.

11. The apparatus of claim 1, wherein the processor is further configured to:
based on the bio-signal that is measured for a first period of time being irregular, control the sensor to increase a measurement time and measure the bio-signal for a second period of time; and
determine whether the bio-signal that is measured for the second period is regular or irregular.

12. The apparatus of claim 1, wherein the bio-information comprises one or more of a blood pressure, a cardiac arrhythmia, a vascular age, skin elasticity, a skin age, an arterial stiffness, an aortic pressure waveform, a stress index, and a degree of fatigue.

13. A method of estimating bio-information, the method comprising:
measuring a bio-signal from an object using a sensor including a single light source and a single light detector detecting light reflected from the object;
decomposing the bio-signal from the single light detector into a plurality of pulse waveforms;
acquiring synchronization information of the plurality of pulse waveforms based on a plurality of slope waveforms corresponding to the plurality of pulse waveforms;
acquiring a synchronization rate of a reference interval based on the synchronization information;
determining whether the bio-signal is regular or irregular based on the synchronization rate of the reference interval; and
estimating the bio-information using the bio-signal based on determining that the bio-signal is regular,
wherein based on determining that the bio-signal is irregular, providing a visual output via a display, the visual output including the bio-signal determined to be irregular together with a regular bio-signal to guide the user to re-measure the bio-signal,
wherein bio-signals from the single light detector are measured from a single point of contact with the object.

14. The method of claim 13, further comprising binarizing the plurality of slope waveforms at each point in time of the reference interval,
wherein the acquiring of the synchronization information comprises acquiring absolute values of averages of the values binarized at each point in time as the synchronization information.

15. The method of claim 14, wherein the acquiring of the synchronization rate of the reference interval comprises acquiring an average of the absolute values in the reference interval among the acquired absolute values as the synchronization rate of the reference interval.

16. The method of claim 13, wherein the estimating of the bio-information comprises determining a representative pulse waveform from among the plurality of pulse waveforms based on determining that the bio-signal is regular, and extracting a feature to be used for bio-information estimation from the determined representative pulse waveform.

17. The method of claim 16, wherein the extracting of the feature comprises extracting the feature by searching an interval of the representative pulse waveform that corresponds to the reference interval.

* * * * *